United States Patent [19]
Patel et al.

[11] Patent Number: 5,843,356
[45] Date of Patent: Dec. 1, 1998

[54] CATHETER TIP MOLD AND CUT PROCESS

[75] Inventors: Jay M. Patel, Palo Alto, Calif.; Dennis Bialecki, Oxford; Joseph J. Chang, Avon, both of Conn.

[73] Assignee: Johnson & Johnson Medical, Inc., Arlington, Tex.

[21] Appl. No.: 773,942

[22] Filed: Dec. 30, 1996

[51] Int. Cl.⁶ .................................................. B19C 37/02
[52] U.S. Cl. ...................... 264/161; 264/296; 264/323; 425/302.1; 425/393
[58] Field of Search .................. 264/159, 161, 264/163, 323, 320, 296; 425/393, 302.1

[56] References Cited

U.S. PATENT DOCUMENTS

| | | | |
|---|---|---|---|
| 2,804,654 | 3/1957 | Sherman | 264/163 |
| 4,404,159 | 9/1983 | McFarlane | 264/296 |
| 4,551,292 | 11/1985 | Fletcher et al. | 264/139 |
| 4,661,300 | 4/1987 | Daugherty | 264/40.6 |
| 4,961,809 | 10/1990 | Martin | 264/322 |
| 5,135,599 | 8/1992 | Martin et al. | 264/322 |
| 5,178,803 | 1/1993 | Tsuchida et al. | 264/323 |
| 5,409,644 | 4/1995 | Martin et al. | 264/322 |
| 5,470,220 | 11/1995 | Potes et al. | 425/216 |
| 5,547,364 | 8/1996 | Wong et al. | 425/384 |
| 5,736,085 | 4/1998 | Brown et al. | 264/161 |

*Primary Examiner*—Jan H. Silbaugh
*Assistant Examiner*—Mark Eashoo
*Attorney, Agent, or Firm*—Joseph F. Shirtz

[57] ABSTRACT

In a first process described a tapered catheter tip is molded by placing a tubular catheter over a mandrel and inserting the mandrel and catheter assembly into a mold having an inner mold surface. The molded catheter with flash is thereafter removed from the mold and the mandrel removed from the catheter. The catheter and flash are inserted into a jig which defines an opening through which the flash extends. The opening is defined by a cutting surface and the flash extends above such cutting surface. A cutter is then moved along the cutting surface in order to sever the flash at precisely the appropriate point along the catheter length to leave a formed trimmed catheter. The catheter is thereafter removed from the jig for further processing.

7 Claims, 1 Drawing Sheet

CATHETER TIP MOLD AND CUT PROCESS

FIELD OF THE INVENTION

The invention relates to a process for forming medical devices and in particular a process for forming tapered tipped catheters.

BACKGROUND OF THE INVENTION

It has long been known to taper the tip of a catheter, in particular, a peripherally inserted intravenous catheter in order to ease the insertion process. It has further been found and many products today have a dual bevel formed at the catheter tip. The first bevel is a taper of approximately 3° and the second bevel is a taper of approximately 27°.

These tips may be formed for example by laser cutting as shown in U.S. Pat. No. 5,425,903 or by molding as shown in U.S. Pat. No. 4,661,300 to Daugherty.

The Daugherty patent shows a molding process in which a single step operation is used to form and clip the catheter. That is, the catheter is placed on a mandrel with the catheter material extending beyond the mandrel and this assembly is then inserted into a heated mold to form the outer surface of the catheter. The mandrel is advanced to a point where it engages the mold surface to clip the flash from the catheter in a single step.

The single step process, however, has significant disadvantages as it provides short tool life in that both the mold and the mandrel are used as cutting devices and therefore must engage and wear upon each other. This means that during usage the outer surface formed on the catheter varies as the contact between the mandrel and the die wears upon the inner surface of the die. Furthermore, tooling must be replaced in order to maintain a sharp edge on the mandrel to provide appropriate cutting action.

SUMMARY OF THE INVENTION

The present invention calls for a process of forming a tip on an intravenous catheter including the steps of mounting a tubular catheter on a mandrel which mandrel extends beyond the catheter end or proposed tip area. A mold having a tapered inner mold surface that compliments the desired outer surface of the finished catheter is heated and the catheter-carrying mandrel is inserted into the mold to engage the catheter material with the inner mold surface. The engagement of the catheter material with the inner mold surface causes the catheter material to soften and conform to the inner mold surface and forms flash which extends beyond the desired catheter tip. The catheter and mandrel are removed from the mold after the material has had an opportunity to cool and thereafter the mandrel is removed from the catheter. Alternatively, this may be done as a single step removing the mandrel from the catheter and thereafter removing the catheter from the mold.

In a second operation, the catheter with flash attached is inserted into a jig having a cutting surface which defines an opening. The insertion of the catheter into the jig permits the flash to extend through the opening beyond the cutting surface. A cutter is moved along the cutting surface and severs the flash which extends above the surface and separates that flash from the remainder of the catheter. This forms a trimmed catheter which is thereafter removed from the jig for further processing.

The jig may be formed to define a passage that terminates in the desired opening. The passage may be complimentary to the outer surface of the catheter to ease in positioning of the catheter with the flash extending an appropriate distance. The cutter may be a single or double blade such as a razor blade in a hand-held operation. The blade may preferably be from about 0.003" to about 0.010" thick and the catheter may be formed of a material such as polytetrafluoroethylene (PTFE) or polyurethane.

BRIEF DESCRIPTION OF THE DRAWINGS

The invention will now be described with reference to the attached drawings wherein.

DESCRIPTION OF THE PREFERRED EMBODIMENTS

Figure 2:
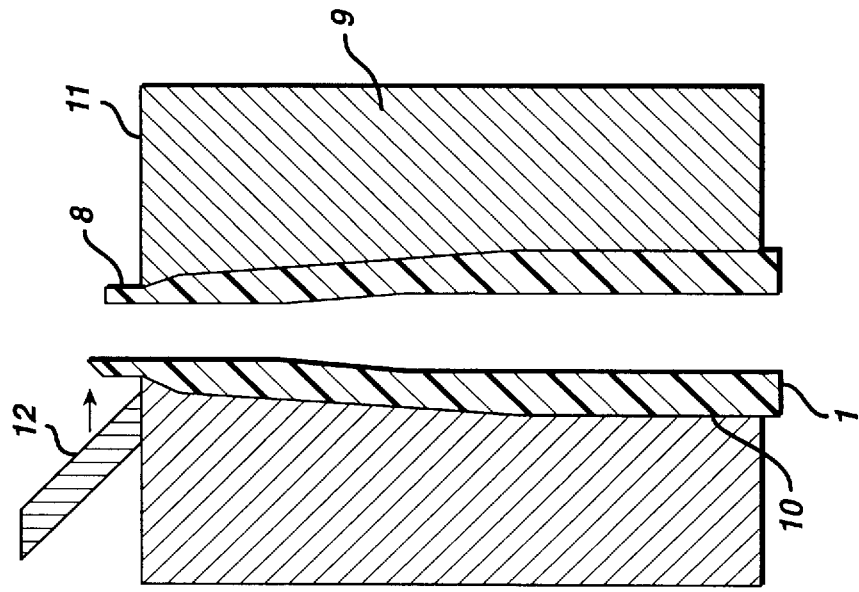
FIG. 2 is a depiction of the cutting jig and cutting process of the present invention.
Figure 1:
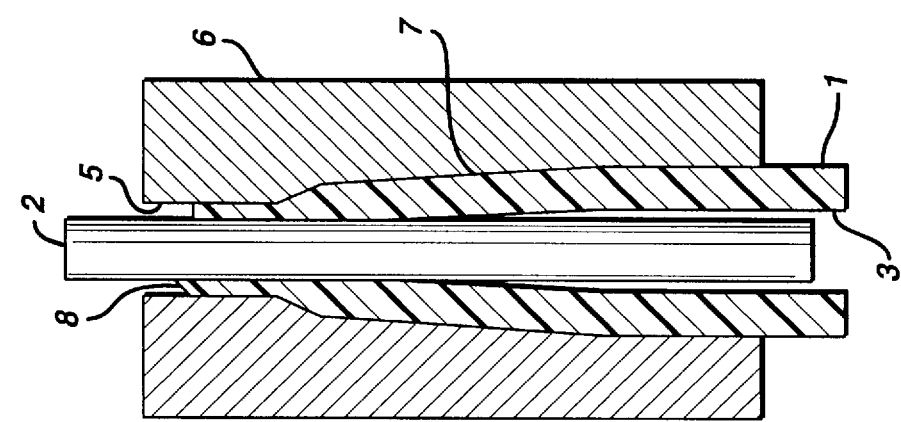
FIG. 1 is a depiction of the molding process of the present invention.

The present invention relates to a simplified and accurate method for forming tips of catheters. In particular, in forming tapered catheter tips it is necessary to both form the taper and remove any flash that may be formed.

In the present process a tubular catheter 1 made of, for example, either polytetrafluoroethylene or polyurethane is placed over a concentric mandrel 2. The mandrel 2 is received within the inner bore 3 of the catheter cannula and extends beyond the end 5 of the catheter. A mold 6 is provided having a tapered inner surface 7 which is complimentary to the outer surface desired on the ultimate catheter. For example, it may be preferred that a shallow taper of approximately 3° is provided along some length of the catheter and a sharper bevel at the very tip of the catheter of for example 27° is provided to draw the catheter surface down to where it would meet a needle cannula passing through the inner bore of the catheter. The mold is heated to a temperature appropriate for softening the catheter material. For example, for a polytetrafluoroethylene catheter of 20 gauge (i.e. 0.045" diameter) this temperature is from about 650° F. to about 750° F. The catheter 1 and mandrel 2 are inserted into the mold 6 in a known manner in order to engage the catheter material with the heated mold surface. The catheter material heats and softens and begins to flow into the space within the mold surrounding the mandrel. A portion of the catheter material flows out of the desired mold area to form a flash tip 8.

It should be noted that the mandrel 2 of the present process passes beyond the flash tip in order to support it such that on cooling a cylindrical piece of flash 8 extends beyond the desired tip of the catheter. This flash 8 will later be removed and extends in such a way as to provide a consistent filling of the mold as well as a consistent portion to be removed by the secondary cutting process.

The mold 6 and catheter 1 are permitted to cool whereupon the catheter 1 and mandrel 2 are withdrawn from the inner mold passage. The mandrel is then withdrawn from within the catheter and the catheter inserted into a female jig 9 (FIG. 2). The female jig 9 has an opening 10 defined therethrough which compliments the desired outer surface of the ultimate catheter. This opening 10 terminates at an upper cutting surface 11 which is positioned with respect to the opening precisely where it is desired that the catheter be cut.

Upon insertion of the catheter 1 within this opening, the flash 8 extends beyond the cutting surface 11 and is exposed outside of the jig. A cutting blade is thereafter run along the cutting surface 11 in order to sever the flash 8 and remove it from the end of the catheter tube. This cutting blade 12 should be as thin as consistent with sufficient strength to cut the catheter material in order to prevent collapsing of the catheter upon itself during the cutting process. It will be easily seen that a dull or thick cutting edge upon passage along the cutting surface would tend to crush the initial side contacted by the blade towards the opposite side thus deforming the catheter and the ultimate cut.

The flash is thereby removed from the tip of the catheter 1 and the catheter removed from the jig 9 for further processing.

The invention has been described in connection with the attached drawings and its preferred embodiments. Minor changes may be made to the invention without exceeding the scope of the contemplated invention.

We claim:

1. A process of forming an intravenous catheter comprising the steps of:
   a) mounting a tubular catheter on a mandrel with the mandrel extending beyond a distal catheter end;
   b) heating a mold having a tapered inner mold surface which includes an area defining a desired catheter tip;
   c) inserting the catheter and mandrel into the mold to engage the catheter with the inner mold surface;
   d) permitting the catheter to be softened and conform to the inner mold surface in said area to form the catheter tip and forming flash extending beyond the catheter tip within the mold,
   e) removing the catheter, with the catheter tip and flash, and mandrel from the mold and the mandrel from the catheter;
   f) then inserting the catheter in a jig having a cutting surface defining an opening such that the flash extends through the opening beyond the cutting surface;
   g) moving a cutter along said cutting surface to sever the flash extending beyond said cutting surface from the catheter to form a trimmed catheter having the tip;
   h) removing the trimmed catheter from the jig.

2. The process according to claim 1 wherein said jig defines a passage terminating in said opening which passage compliments the outer surface of the catheter in order to accurately position the catheter for trimming.

3. The process according to claim 1 wherein the cutter is a single or multiple blade.

4. The process according to claim 3 wherein said blade is from about 0.003" to about 0.010" thick.

5. The process according to claim 1 wherein said cutter comprises a razor blade that is manually moved along said surface to sever said flash.

6. The process according to claim 1 wherein said catheter is made of polytetrafluoroethylene material and the mold is heated from about 650° F. to about 750° F.

7. The process according to claim 1 wherein said catheter is formed of polyurethane material and said mold is heated from about 450° F. to about 550° F.

* * * * *